United States Patent [19]
Seeger et al.

[11] Patent Number: 5,940,681
[45] Date of Patent: Aug. 17, 1999

[54] METHOD AND APPARATUS FOR AUTOMATICALLY CHECKING POSITION DATA OF J-LEADS

[75] Inventors: Hartmut Seeger, Denzlingen; Bernd Sommer, St. Aubine, both of Germany

[73] Assignees: Micronas Intermetall GmbH, Freiburg, Germany; Innovative Technology for Vision, Inc., Saint Blaise, Switzerland

[21] Appl. No.: 08/989,274

[22] Filed: Dec. 12, 1997

[30] Foreign Application Priority Data

Dec. 14, 1996 [DE] Germany ............... 196 52 124

[51] Int. Cl.⁶ ............... G01R 31/26; H01L 21/66
[52] U.S. Cl. ............... 438/16; 438/14; 438/15
[58] Field of Search ............... 438/16, 15, 14

[56] References Cited

FOREIGN PATENT DOCUMENTS 4003983  9/1990  Germany .
4032327  11/1990  Germany .

OTHER PUBLICATIONS

German Search Report for 196 52 124.6, dated Aug. 8, 1997.

Primary Examiner—Kevin M. Picardat
Assistant Examiner—Dever Collins
Attorney, Agent, or Firm—Arthur L. Plevy

[57] ABSTRACT

There is disclosed a method for automatically checking position data of J-leads at a semiconductor component enclosed in a housing with respect to a plane parallel to the bottom side of the housing. The bottom side of the housing is illuminated by light from an illuminator at at least one reproducible angle. The light reflected from the bottom side of the housing and the leads at essentially right angles is picked up by a camera with high resolution. The image signals of the camera are fed to an image signal processing device, and at least one data record with an indicator assigned to the semiconductor component is stored. From the image signals, position data of the leads are determined. Any deviation of the position data from predetermined nominal values is determined by comparing the position data with reference data.

16 Claims, 2 Drawing Sheets

METHOD AND APPARATUS FOR AUTOMATICALLY CHECKING POSITION DATA OF J-LEADS

FIELD OF THE INVENTION

This invention relates to a method for checking position data for component terminals and more particularly to a method for automatically checking position data of J-leads at a semiconductor component enclosed in a housing.

BACKGROUND OF THE INVENTION

Leads serve to connect semiconductor components to the outside world. They protrude from the semiconductor housing and are bent to a J shape, so that they extend essentially underneath the housing of the semiconductor component. The semiconductor component is mounted on a printed circuit board by placing the leads on pads of the circuit board and soldering them to the pads.

The J-leads are formed by stamping processes. In such processes, faults may occur, particularly due to foreign matter in the die. Since, after the component has been soldered on, such faults can no longer be corrected, because the leads are underneath the component, the leads, particularly their position data, need to be checked directly after the stamping processes. It is particularly important to check the position data in a plane parallel to the bottom side of the housing (xy-plane) for colinearity. Undesired displacements of the leads in the xy-plane may be caused by deformations of the leads. A displacement of the leads in the xy-plane may also be present if the leads are coplanar, i.e., if their respective lowest points are spaced the same distance from the bottom side of the housing. This deformation is also called "bow-in" or "bow-out". Therefore, it is necessary to check position data of the leads in the xy-plane, i.e., for colinearity, independently of a check for coplanarity. Conventional automatic methods, such as transmitted-light measurement techniques, are unsuitable, since the Y-leads disappear for the most part under the opaque component. In practice, therefore, a manual visual inspection is carried out. To do this, several components are arranged along a straight line, for example. The observer looks at each component to see whether the individual leads are spaced approximately the same distance from the straight line. Those components which, in his or her view, have leads with excessive deviations in the xy-plane are then discarded. The reliability of the selection is thus dependent on the observer's watchfulness. Accordingly, a method for automatically checking position data of J-leads at a semiconductor component is highly desirable.

SUMMARY OF THE INVENTION

The object of the invention is to provide a method and an apparatus for automatically checking position data of J-leads of semiconductor components.

This object is attained by a method for automatically checking position data of J-leads at a semiconductor component enclosed in a housing with respect to a plane parallel to the bottom side of the housing, the housing being made of a light-absorbing material, and the leads extending from a side surface of the housing to the bottom side of the housing, comprising the steps of: feeding the semiconductor component to a measurement setup in which the bottom side of the housing is illuminated by light from an illuminator at at least one reproducible angle of illumination, particularly at a substantially right angle; picking up the light reflected from the bottom side of the housing and the leads at essentially right angles by means of a camera with high resolution; feeding the image signals of the camera to an image signal processing device; storing at least one data record with an indicator assigned to the semiconductor component; determining position data of the leads from the image signals; and determining any deviation of the position data from predetermined nominal values by comparing the position data with reference data. An apparatus for automatically checking position data of J-leads is also disclosed.

BRIEF DESCRIPTION OF THE DRAWINGS

The invention will now be explained in more detail with reference to the accompanying drawings, in which.

DETAILED DESCRIPTION OF THE INVENTION

Figure 1:
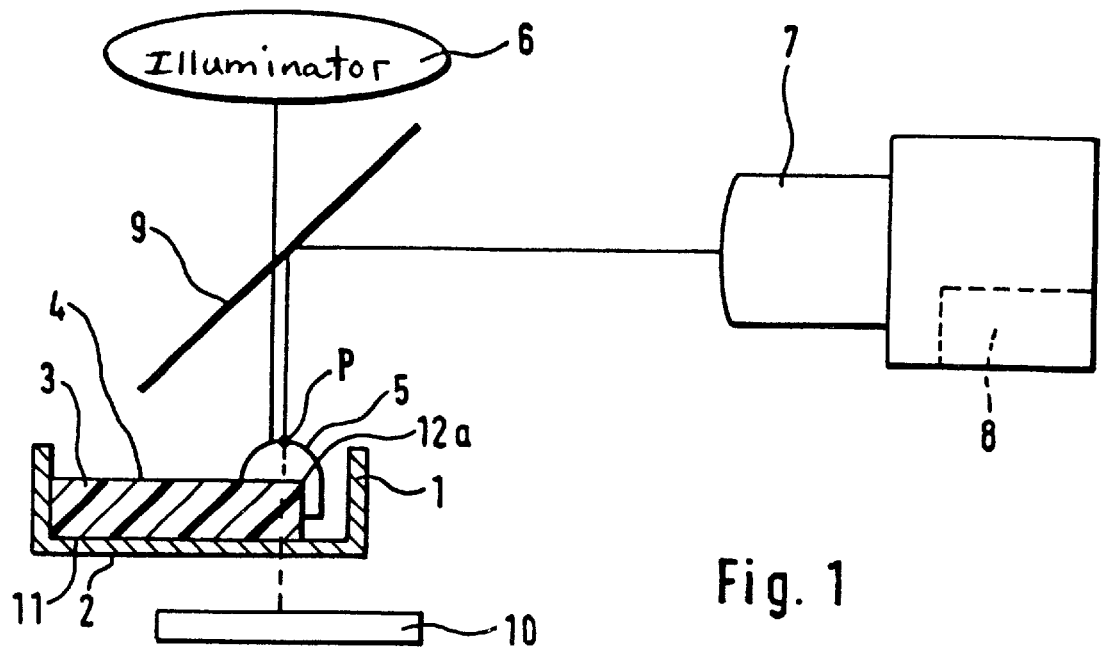
FIG. 1 shows a first embodiment of an apparatus according to the invention.

Before embarking on a detailed discussion, the following should be understood. At J-leads, the light is reflected essentially from that point perpendicular to the bottom side of the housing where the curvature of the lead has a tangent parallel to this bottom side. This point corresponds to the lowest point of the lead, i.e., the point farthest away from the bottom side of the housing. At this point, the lead is placed on a board during soldering. From the other points of the lead, the light is reflected in other directions, since at those points the tangent is inclined to the bottom side of the housing of the component. Since the housing is made of a light-absorbing material, only very little light is reflected from it. Thus, the light reflected in a direction perpendicular to the bottom side of the housing shows the position of the leads, more correctly the position of the lowest portion of the leads in the xy-plane. The camera signals thus obtained are processed and stored as a data record in an image signal processing device. To record the image, a CCD camera can be used. By comparing the position data of the leads derived from the image signals with reference data, it is determined to what extent the position data of each of the leads deviate from a predetermined nominal value. With this method, an image can be produced of the entire bottom side of the housing with all leads. Since each component is examined as to whether it meets the required values, each component for which that is not the case can be discarded.

Preferably, the light is directed to the semiconductor component at a substantially right angle of illumination.

Advantageously, the semiconductor components whose position data deviate from the predetermined nominal values are discarded automatically. Then the components which were not discarded can be automatically packed for shipment. The automatic checking of position data of the leads in accordance with the invention increases the reliability of the detection of components which deviate from the nominal values, and is substantially faster than conventional techniques.

Advantageously, the top side of the housing is illuminated with a light source, the light scattered into the camera is measured, and the position of at least one edge of the housing is determined from the image signal data record thus obtained, and stored. Since the housing is made of a light-absorbing material, indirect backlighting can be produced by the light source, whereby an exact shadow projection image of the housing is produced in the camera. This makes it possible to precisely determine the edges of the housing and, thus, the position of the component in the measuring position. The housing of the component is frequently made of black epoxy resin.

Furthermore, the image signals can be compared with a predetermined threshold value, and the image signal greater than threshold value can be used to determine reflex areas by which the respective positions of the leads in a plane parallel to the bottom side of the housing are determined. In this manner, light which does not belong to the reflex areas representing the leads is excluded, so that an image with sharper contours is produced. It is then possible to determine the respective centers of gravity $r_{cm}$ of the reflex areas. These represent the respective lowest points of the leads. The center of gravity can be determined from the following formulas:

$$\vec{r}_{cm} = \frac{\int \vec{r} dm}{\int dm} = \frac{1}{N} * \begin{Bmatrix} \sum_{i=1}^{N} x_i \\ \sum_{i=1}^{N} y_i \end{Bmatrix}$$

In one embodiment of the invention, the positions of the reflex areas or of the centers of gravity of the reflex areas relative to an edge of the housing is determined. The distance from the reflex areas to the housing edge and its deviation from a specified nominal value can be determined. Semiconductor components are discarded if this distance is outside the tolerance specified for the component.

In another embodiment of the invention, the positions of the reflex areas or of the centers of gravity of the reflex areas relative to each other are determined, particularly the distance of a reflex area from the adjacent reflex areas or the distance of a reflex area from a straight line extending through the reflex areas parallel to an edge of the housing. Since the leads are usually located on a straight line parallel to an edge of the housing, it is possible to determine from the distance to the adjacent reflex areas the deviation from the positions of the leads in the xy plane, and from the distance of a reflex area to the straight line extending through all reflex areas the deviation in a direction perpendicular to the straight line. By calculation using a mathematical method, the straight line can be placed through the reflex areas or through those reflex areas which deviate only little from a straight line.

As reference data, the stored image signals of a preceding measurement on one housing with correctly arranged leads or average values of the image signals of preceding measurements on two or more such housings can be used.

In a further preferred embodiment of the invention, light is directed to the housing and the leads successively at different angles of illumination, the light reflected from the housing and the leads at right angles is picked up by the camera, the image data produced per angle of illumination are stored as respective data records, and shape data of the leads are determined from the data records associated with a semiconductor component, and compared with reference data. In this manner, the arc profile of each lead can be measured accurately. From this, further information about the quality of the leads, particularly about the planarity of the contact areas, can be derived. From the shape of the leads, conclusions can also be drawn regarding their mechanical stability. Since the light of the light sources is incident on the leads at different angles with respect to the vertical axis, light is reflected to the camera from different curved areas of the lead. Since the positions of the respective light sources are known, the angle of inclination of the lead at the point where the light was reflected can be determined in the image signal processing device. Thus, one angle of inclination of the lead per light source is obtained at the point producing the light reflex, so that the curvature of the lead can be determined. By comparing the calculated profile with a good reference profile, it can be determined whether the component meets specified requirements.

FIG. 1 shows an apparatus according to the invention in a schematic cross-sectional view. On a transfer rail 1, a housing 3, which contains a semiconductor device (not shown), is positioned in a measuring position 2. The housing 3 is arranged with the bottom side 4 up. One of the J-leads 5 is shown, which extends from a side surface of the housing 3 to the bottom side 4 of the housing. This is a correct lead 5, i.e., a lead which is not deformed. In the embodiment shown, the leads 5 are arranged one behind the other along one edge of the housing 3. The apparatus according to the invention is also suitable for measuring housings where the leads are provided along two or more edges, using the same method.

By means of an illuminator 6 provided above the measuring position 2, light is directed to the bottom side 4 of the housing 3 at a predetermined angle of illumination, here an angle normal to the bottom side. The housing 3 of the semiconductor device is made of light-absorbing material, generally of black epoxy, and the leads 5 are made of a light-reflecting material, namely an electrically conductive material. The light incident on the housing 3 and the leads 5 is therefore reflected by the leads 5. A camera 7 with an image signal processing device 8 is so positioned that the light reflected from the housing 3 and the leads 5 at right angles is directed via a beam splitter 9 into the camera 7. The light reflected from the lead 5 into the camera 7, which is reflected in a direction perpendicular to the plane of the measuring position 2 or the bottom side 4 of the housing 3, is reflected from a point P of the lead 5 at which the tangent is horizontal, i.e., parallel to the bottom side 4 of the housing 3. Thus, the light reflex measured by the camera 7 is formed by reflection of the lowest point P of the lead 5. At this lowest point P, the lead 5 will later bear on a support, particularly on a printed circuit board. It is important that the lowest points P of a row of leads 5 lie precisely in a plane parallel to the bottom side 4 of the housing 3. The required precision depends on the tolerances specified for the intended application of the semiconductor component. The image signals of the camera 7 are processed in the image signal processing device 8.

Also provided is a light source 10 with which the front side 11 of the housing 3 is illuminated. This requires that, at least in the measuring position, the bottom of the transfer rail 1, on which the housing 3 rests, be made of a transparent material. Through this backlighting, a shadow projection of the light-absorbing housing 3 is obtained. The camera 7 thus takes a shadowgraph of the housing 3. From the image data thus obtained, the position of the component on the transfer rail 1 can be determined with the image signal processing device 8. The circumferential edge of the housing 3 can be measured by precisely measuring a number of predefined points of the edge 12 of the housing 3 using the software provided in the image signal processing device 8. The contour determined therefrom is a reference from which reference data for the further measurement operations can be generated. The positions of the contact points P of the leads 5 relative to an edge 12 of the housing 3 can be precalculated as reference data, including a tolerance range.

Figure 2:
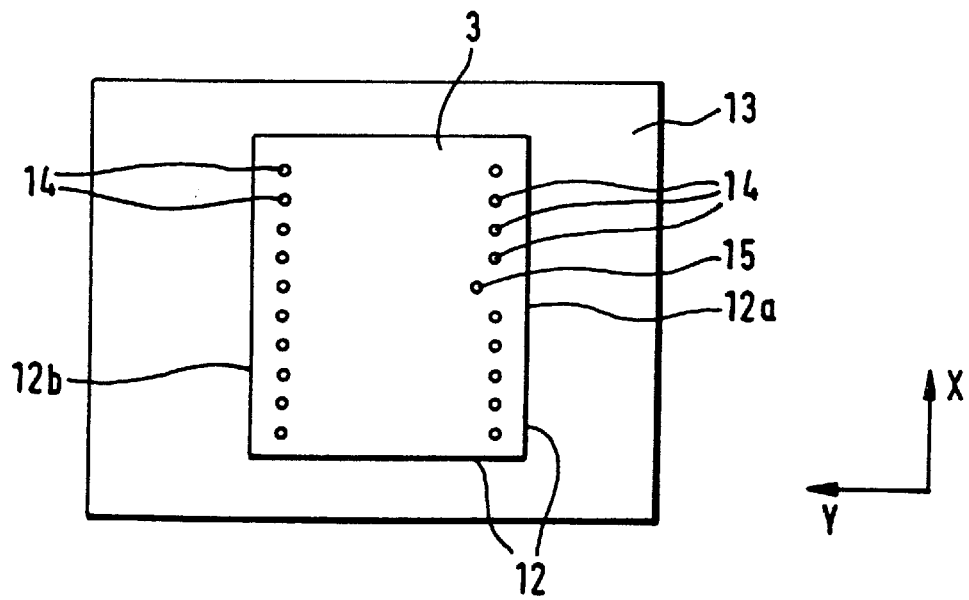
FIG. 2 shows an image, produced by the method according to the invention, of the bottom side of the housing with the leads.

The result of a measurement operation is illustrated in FIG. 2. A housing 3 of a semiconductor component is shown which has two rows of leads 5, one along each of two opposite edges 12a, 12b. On a background 13, the silhouette of the entire circumferential edge 12 of the housing 3 can be seen. The position data of the circumferential edge 12 are obtained from the measurement with backlighting by means of the light source 10. With the episcopic illumination by means of the illuminator 6, reflex areas 14 are produced which represent the positions of the contact points P of the leads 5. From the measurement of the circumferential edge 12 of the housing 3, the positions of the contact points P of the leads 5 in the xy-plane, including a predetermined tolerance range, can be calculated with the image signal processing device 8. By comparing the measured data of the reflex areas 14 with the values thus calculated, it can be determined whether the component in the housing 3 can be used for the intended application or has to be discarded. The data obtained from the measurement with backlighting and episcopic illumination can be processed in such a way that they are presented together in one picture, as is shown in FIG. 2.

In the representation of the measurement result of FIG. 2 it can be seen that the reflex areas 14, and thus the contact points P, along the edge 12b are essentially in a row, i.e., there is no major deviation in the y-direction. Along the edge 12a, there is a reflex area 15 which is clearly out of line with the other reflex areas 14 in the y-direction. The associated semiconductor component would have to be discarded. The discarding can be done in a variety of ways. It can be done automatically by providing on or behind the transfer rail an appropriate device which is supplied with the respective measurement signals. The device may be, for example, a flap to be opened for components to be discarded. It is also possible, however, to provide the components to be discarded with marks and subsequently check the marks.

Figure 3A:
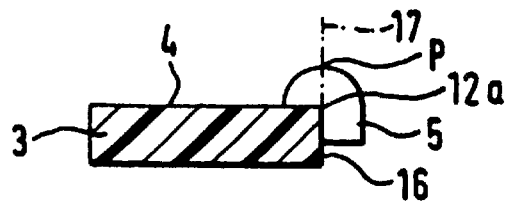
FIG. 3a shows a cross section of a housing of a semiconductor component with a correct J-lead.

FIG. 3 illustrates how a displacement of the contact point P of a lead 5 in the xy-plane may be caused. FIG. 3a shows a cross section of a housing 3 which has a correct J-lead 5. The lead 5 extends from one side surface 16 of the housing 3 to the bottom side 4 of the latter. In this example, the lead is so arranged that the contact point P is exactly above the edge 12a of the component 3. In that case, a projection line 17 normal to the bottom side 4 of the housing 3 through the contact point P ends exactly on the edge 12a of the housing 3.

Figure 3B:
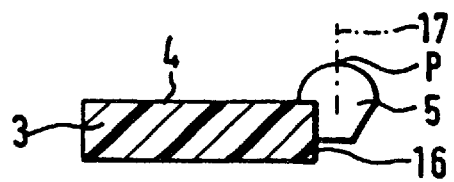
FIG. 3b shows a J-lead bent outward.

In FIG. 3b, the lead at the housing 3 is bowed outward. Such deformations may be caused in the stamping operations required to form the leads 5. In such a case, the contact point P is on a level with the contact point P of the correct lead 5 of FIG. 3a in the z-direction, i.e., in the direction perpendicular to the xy-plane. It is displaced only in the xy-plane, in this example in the y direction. As a result of such a fault in the lead 5, this lead will not bear on the associated pad of a printed circuit board and thus cannot be soldered on. This fault can be detected only by a measurement in the xy-plane. By a height measurement in the z-direction, it would not be detected. In that case, the projection line 17 through the point P ends outside of the housing 3.

Figure 3C:
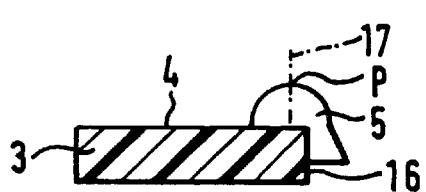
FIG. 3c shows a J-lead bent inward.

FIG. 3c shows the same housing 3 with a lead 5 which is bowed inward. In that case, the contact point P is displaced inward in the y-direction. A projection line 17 through the contact point P ends in the interior of the housing 3. In that case, too, there is no deformation of the lead 5 in the z-direction. As in FIG. 3c, the fault can only be determined by measuring the projection of the contact P in the xy-plane.

Figure 4:
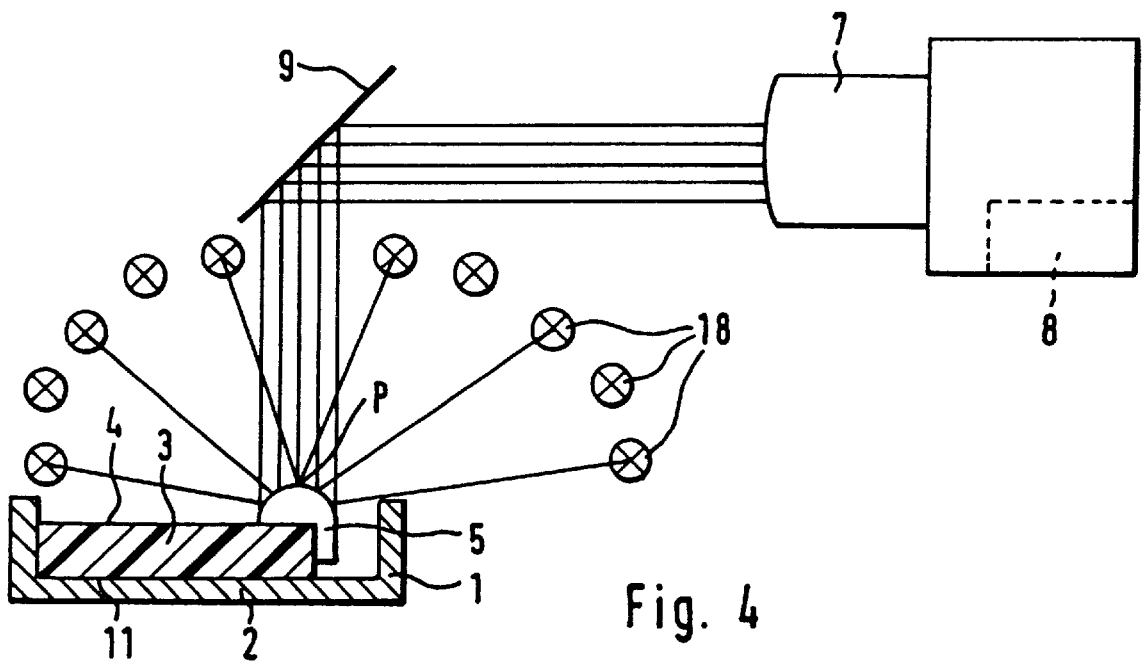
FIG. 4 shows a second embodiment of the apparatus according to the invention.

FIG. 4 shows another embodiment of the invention. Analogously to FIG. 1, a housing containing a semiconductor component is so arranged on the transfer rail 1 that its top side 11 rests on the transfer rail in a measuring position 2, with the bottom side 4 of the housing 3 pointing upward. The light reflected from leads 5 (of which one can be seen) at essentially right angles is directed via a beam splitter 9 into a camera 7. The latter includes an image signal processing device 8 in which the image signals produced by a shot taken with the camera 7 are stored and processed. The embodiment of FIG. 4 differs from that of FIG. 1 in that several single sources of illumination 18 are provided which each direct one light beam to the lead at a given angle. The single sources of illumination 18 are arranged essentially along a circular arc around the lead 5 and spaced at approximately equal intervals. Since the angles of incidence and the angles of reflection are fixed, the slopes of the tangents at different points along the lead 5 can be measured. From this, an accurate analysis of the arc profile of the lead 5 can be deduced. The shape of the lead 5 gives information about the quality and stability of the lead and about the planarity of the contact area at the contact point P. The arc profile also shows, for example, whether pit holes are present in the metal as a result of photolithographic and etching processes. Such holes would make a lead very unstable. Furthermore, an irregular curvature of the lead 5 reduces the mechanical rigidity of the latter, so that it may be deformed when being soldered to the printed circuit board. The criteria of the arc profile of a lead can be specified according to the requirements placed on the semiconductor component. In the image signal processing device 8, the measured and processed values can be compared with predetermined reference values. If deviations lie outside predetermined tolerance ranges, the components can be discarded as described above. Also provided is a control facility (not shown) with which the single sources of illumination 18 can be activated in succession and the light reflected at the respective leads 5 is picked up by the camera 7 and can be processed in the image signal processing device 8. This measurement setup can be used both alone and in combination with the setup of FIG. 1.

What is claimed is:

1. A method for automatically checking position data of J-leads (5) at a semiconductor component enclosed in a housing (3) with respect to a plane parallel to the bottom side (4) of the housing (3), the housing (3) being made of a light-absorbing material, and the leads (5) extending from a side surface (16) of the housing (3) to the bottom side (4) of the housing (3), said method comprising the steps of:

feeding the semiconductor component to a measurement setup in which the bottom side (4) of the housing (3) is illuminated by light from an illuminator (6, 18) at least one reproducible angle of illumination, particularly at a substantially right angle;

picking up the light reflected from the bottom side (4) of the housing (3) and the leads (5) at essentially right angles by means of a camera (7) with high resolution;

feeding the image signals of the camera (7) to an image signal processing device (8); storing at least one data record with an indicator assigned to the semiconductor component;

determining position data of the leads (5) from the image signals; and determining any deviation of the position data from given nominal values by comparing the position data with reference data.

2. The method according to claim 1, further comprising the step of automatically discarding the semiconductor components whose position data deviate from the given nominal values.

3. The method according to claim 1, further comprising the steps of illuminating the top side (11) of the package (3) by means of a light source (10), measuring the light scattered into the camera (7), and determining the position of at least one edge (12a, 12b, 12) of the housing from the image signal data record thus obtained, and stored.

4. The method according to claim 3, wherein the image signals are compared with a given threshold value, and those image signals greater than the threshold value are used to determine reflex areas by which the positions of the respective leads (4) in a plane parallel to the bottom side (11) are determined.

5. The method according to claim 4, further comprising the step of determining the respective centers of gravity of the reflex areas (14).

6. The method according to claim 5, further comprising the step of:

determining the positions of the reflex areas (14) or of the centers of gravity of the reflex areas (14) relative to an edge (12a, 12b) of the housing (3).

7. The method according to claim 5, further comprising determining the positions of the reflex areas (14) or of the centers of gravity of the reflex areas (14) relative to each other, particularly the distance from a reflex area (14) to the adjacent reflex areas (14) or the distance from a reflex area (14) to a straight line extending parallel to an edge (12a, 12b) of the housing (3) through the reflex areas (14).

8. The method according to claim 7, further comprising the step of:

using as reference data, the stored image signals of a preceding measurement on one housing (3) with correctly arranged leads (5) or average values of image signals of preceding measurements on a plurality of housings (3) with correctly arranged leads (5).

9. The method according to claim 8, further comprising the steps of:

directing the light to the housing (3) and the leads (5) successively at different angles of illumination, the respective light being reflected from the housing (3) and the leads (5) being picked up by the camera (7), wherein the image data generated per angle of illumination are stored as respective data records, and shape data of the leads (5) are determined from the data records associated with a semiconductor component, and compared with reference data.

10. A method for automatically checking position data of J-leads of a semiconductor component enclosed in a housing having an under-side, said method comprising the steps of:

illuminating said under-side of said housing and said J-leads;

picking up light reflected from said under-side of said housing and said J-leads;

forming at least one image signal from said light picked up; and, determining position data of said J-leads from said at least one image signal.

11. The method of claim 10, further comprising the step of determining deviation of said position data from nominal values by comparing said position data with reference data.

12. The method of claim 11 further comprising the step of comparing said deviation with at least one threshold.

13. The method of claim 12, further comprising the step of automatically discarding said semiconductor component if said deviation exceeds said threshold.

14. The method of claim 10, wherein said step of picking up light reflected further comprises the step of picking up light reflected at a substantially right angle from said under-side of said housing.

15. The method of claim 10, wherein said housing further comprises a top-side being oppositely disposed from said under-side, said method further comprising the steps of:

illuminating said top-side of said housing;

identifying at least one boundary of said housing; and, determining boundary-position data from said at least one boundary.

16. The method of claim 15, further comprising the step of determining deviation of said position data from nominal values by evaluating said position data and said boundary-position data with reference data.

* * * * *